United States Patent
Lin et al.

(10) Patent No.: US 8,235,905 B2
(45) Date of Patent: Aug. 7, 2012

(54) SYSTEM AND METHOD FOR AUTOMATIC ULTRASOUND IMAGE OPTIMIZATION

(75) Inventors: Feng Lin, Niskayuna, NY (US); Mirsaid Seyed-Bolorforosh, Albany, NY (US)

(73) Assignee: General Electric Company, Niskayuna, NY (US)

( * ) Notice: Subject to any disclaimer, the term of this patent is extended or adjusted under 35 U.S.C. 154(b) by 472 days.

(21) Appl. No.: 12/471,732

(22) Filed: May 26, 2009

(65) Prior Publication Data

US 2010/0305441 A1    Dec. 2, 2010

(51) Int. Cl.
*A61B 8/00*    (2006.01)
(52) U.S. Cl. .................... 600/443; 600/442; 600/458
(58) Field of Classification Search ................ 600/437, 600/442, 443, 458; 73/631
See application file for complete search history.

(56) References Cited

U.S. PATENT DOCUMENTS

| | | | |
|---|---|---|---|
| 6,120,446 A | 9/2000 | Ji et al. | |
| 6,699,189 B1 | 3/2004 | Lin et al. | |
| 6,733,454 B1 | 5/2004 | Bakircioğlu et al. | |
| 6,743,174 B2 | 6/2004 | Ng et al. | |
| 2005/0033175 A1* | 2/2005 | Lee et al. | 600/453 |

FOREIGN PATENT DOCUMENTS

| | | |
|---|---|---|
| EP | 0533976 A1 | 3/1993 |
| WO | 2007/072362 A2 | 6/2007 |

* cited by examiner

*Primary Examiner* — Brian Casler
*Assistant Examiner* — Rajeev Siripurapu
(74) *Attorney, Agent, or Firm* — Marie Claire B. Maple

(57) ABSTRACT

A method for automatic image optimization in ultrasound imaging of an object is provided. The method includes transmitting a first ultrasound signal into the object, wherein the signal has a plurality of first signal parameters. The method also includes receiving a first set of electrical signals representing reflections of the first ultrasound signals from the object and processing the first set of electrical signals into a first image. The method evaluates an image quality cost function for the first image to produce a first image quality metric and determines a second plurality of signal parameters based upon the first image quality metric. Similarly, the method includes transmitting a second ultrasound signal into the object, wherein the signal has the second plurality of signal parameters and receiving a second set of electrical signals representing reflections of the second ultrasound signal from the object and processing the second set of electrical signals into a second image. The method also includes evaluating an image quality cost function for the second image to produce a second image quality metric. The method further includes comparing the first image quality metric and the second image quality metric to determine whether a maximized image quality metric has been reached and assigning multiple signal parameters that produced the maximized image quality metric as optimum parameters. The method further includes imaging and displaying the object using an ultrasound signal having the optimum parameters.

14 Claims, 3 Drawing Sheets

SYSTEM AND METHOD FOR AUTOMATIC ULTRASOUND IMAGE OPTIMIZATION

BACKGROUND

The invention relates generally to ultrasound imaging systems, and more particularly, to automatic image optimization in such systems.

The use of ultrasound to produce images for medical diagnosis has become common as a result of its nonionizing nature, the ability to produce images resulting from the inherent differences in mechanical properties of various soft tissues, and advances in technology. Current applications include examination of the heart, abdomen, and fetus. In most areas, diagnosis is now generally based on the size, position, contour, and motion of structures as well as on their relative transmission and reflection properties.

In general, for a typical ultrasound scanner, a user needs to perform multiple operations to obtain optimized images, which is time-consuming and operator dependent. Furthermore, an inexperienced user may generate suboptimal images increasing risk of an incorrect diagnosis.

A common practice is to pre-set imaging parameters for each ultrasound probe and each clinical application. In this case, the scanner will have a good performance on an average patient without user adjustment. However, such an approach does not handle patient dependency, which is critical for ultrasound imaging.

Automatic gain optimization has also been widely implemented in ultrasound scanners. The acquired images are analyzed and local amplitude is adjusted to obtain optimal image brightness, contrast, and uniformity. However, such a technique only addresses a portion of the image optimization issues and does not account for fundamental beamforming parameters, such as, for example, frequency, aperture size, which are also critical to image quality.

Therefore, an improved ultrasound imaging system is desirable to address one or more of the aforementioned issues.

BRIEF DESCRIPTION

In accordance with an embodiment of the invention, a method for automatic image optimization in ultrasound imaging of an object is provided. The method includes transmitting a first ultrasound signal into the object, wherein the signal has a plurality of first signal parameters. The method also includes receiving a first set of electrical signals representing reflections of the first ultrasound signals from the object. The method further includes processing the first set of electrical signals into a first image. The method also includes evaluating an image quality cost function for the first image to produce a first image quality metric. The method also includes determining a second plurality of signal parameters based upon the first image quality metric. The method further includes transmitting a second ultrasound signal into the object, wherein the signal has the second plurality of signal parameters. The method also includes receiving a second set of electrical signals representing reflections of the second ultrasound signal from the object. The method further includes processing the second set of electrical signals into a second image. The method also includes evaluating an image quality cost function for the second image to produce a second image quality metric. The method further includes comparing the first image quality metric and the second image quality metric to determine whether a maximized image quality metric has been reached. The method also includes assigning a plurality of signal parameters that produced the maximized image quality metric as optimum parameters. The method further includes imaging the object using an ultrasound signal having the optimum parameters. The method also includes displaying a resulting image of the object based upon the ultrasound signal with the optimum parameters.

In accordance with another embodiment of the invention, a system for automatic image optimization in ultrasound imaging of an object is provided. The system includes an ultrasound transducer acoustically coupled to the object, wherein the ultrasound transducer is configured to transmit a first ultrasound signal and a second ultrasound signal into the object, wherein the first ultrasound signal and the second ultrasound signal comprise a first set of signal parameters and a second set of signal parameters respectively. The ultrasound transducer also converts a first set of reflected ultrasound signals and a second set of reflected signals from the object into a respective first set of electrical signals and a second set of electrical signals. A processor coupled to the ultrasound transducer processes first set of electrical signals and the second set of electrical signals into a first image and a second image. The processor evaluates an image quality cost function for the first image and the second image to produce a first image quality metric and a second image quality metric. The processor also determines a second set of signal parameters based upon the first image quality metric. The processor further compares the first image quality metric and the second image quality metric to determine whether a maximized image quality metric has been reached. Multiple parameters that produce a maximized image quality metric are assigned as optimum parameters. The object is further imaged using an ultrasound signal having the optimum parameters. A display monitor is configured to display a resulting image of the object based upon the imaged object from the ultrasound signal with the optimum parameters.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments of the invention are directed to a system and method for ultrasound image optimization. The technique includes an image quality cost function that dynamically enables optimization of image quality by adjusting ultrasound imaging parameters such as beamforming parameters and signal processing parameters. As used herein, the term 'beamforming' refers to a technique used for directional signal transmission or reception. A beamforming process controls the phase and relative amplitude of the signal generated at multiple ultrasound transducer elements before they combine into an ultrasound beam, in order to create a pattern of constructive and destructive interference in a wavefront. Non-limiting examples of beamforming parameters may include transmit frequency, transmit/receive aperture size, transmit/receive apodization, number of focal zones, and depths of the focal zones.

Figure 1:
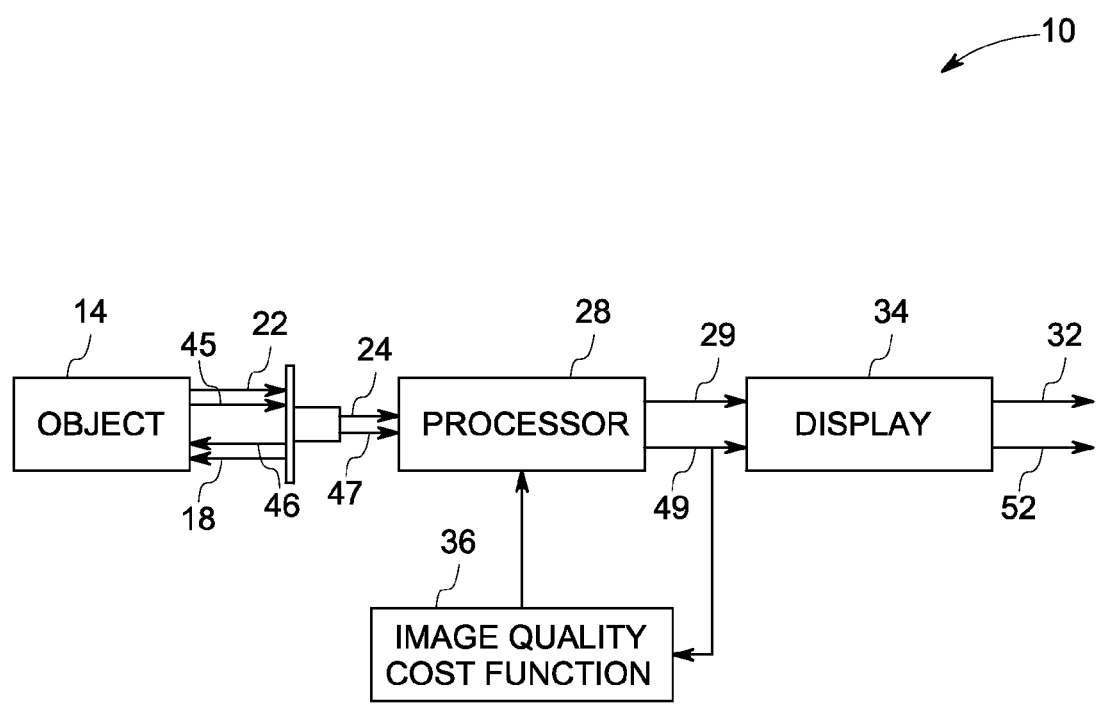
FIG. 1 is a block diagram representation of a system for ultrasound imaging of an object in accordance with an embodiment of the invention.

FIG. 1 is a block diagram representation of a system 10 for ultrasound imaging of an object 14, for example, a living organism. The system 10 includes an ultrasound transducer 16 acoustically coupled to the object 14. In one embodiment, the ultrasound transducer 16 includes a handheld ultrasound transducer. The ultrasound transducer 16 transmits a first ultrasound signal 18 into the object 14. The first ultrasound signal 18 includes multiple first signal parameters. A first set of reflected ultrasound signals 22 are converted into a first set of electrical signals 24. A processor 28 coupled to the ultrasound transducer 16 processes the first set of electrical signals 24 outputting processed image data 29 into a first image 32 displayed by a display monitor 34. The processor 28 evaluates an image quality cost function referenced by numeral 36 for the first image 32. In a particular embodiment, image data is processed at various locations of a signal chain before a final image is generated. The image data may be either RF data or amplitude-only signal. In another embodiment, the final image is processed to obtain image quality information, but it is typically less reliable. It should be noted that the signal parameters are associated with transmission, receiving and during signal processing.

A second set of parameters is determined based upon a first image quality metric of the first image 32. The process is repeated for a second set of ultrasound signals 46 having the second set of parameters. A second set of reflected ultrasound signals 45 are transmitted by the ultrasound transducer 16 as second set of electrical signals 47. The signals 47 are output by the processor 28 as image data 49 to obtain a resulting second image 52. The processor 28 computes a second image quality metric for the second image 52 and further compares the second image quality metric to the first image quality metric to determine if a maximized image quality has been reached. There are various scenarios wherein a maximized image quality is reached. In one embodiment, a second image may have a quality worse than a first image. In another embodiment, a plot of successive image quality metrics stops increasing. In yet another embodiment, two calculated image quality metrics have a difference less than a predetermined threshold. In another embodiment, a threshold of maximal number of iterations allowed is reached.

In one embodiment, when the image quality has been maximized, multiple parameters associated with the maximized image quality metric are computed and assigned as optimum parameters and an optimal image is displayed on the display monitor 34. As used herein, the term 'optimal image' refers to an image produced by parameters that have been determined as optimum by an objective measure of a quality of the image. In an alternative embodiment, when the image quality metric has not been maximized, the entire process is repeated until a maximized image quality is reached. In one embodiment, the processor adjusts beamforming parameters such as, but not limited to, at least one of frequency, transmit pulse length, nominal sound speed, a transmit aperture size, a receiving aperture size, a pulse repetition frequency, beam line density, number of focal zones and positions of focal zones. The beamforming parameters are software-configurable and hence may be performed fully automatically without user intervention. In an exemplary embodiment, the aperture size is actually an active aperture size that is used for the transmit or receive and is controlled electronically. In another embodiment, the processor adjusts image processing parameters such as, but not limited to, receive filter, gain partition and dynamic range compression.

The image quality factors are fundamentally coupled. Improving one factor may have an inverse effect on another factor. For example, one can improve spatial resolution of an ultrasound image by increasing the transmit frequency. That, however, will reduce the penetration. In another exemplary embodiment, one can improve frame rate of an ultrasound image by reducing the beam line density. That, however, will reduce the spatial resolution. Hence, a cost function is an optimal tool to evaluate the effect of the image quality factors. The image optimization problem is transformed to a mathematical problem of maximizing a cost function. The image quality cost control function as a function of image parameters may be expressed as:

$$\text{Cost}(x) = \Sigma c Y(x)$$

wherein vector Y represents image quality factors, vector X represents image parameters that effect image quality and c is a vector of weighting coefficients. The coefficients may be nonlinear. The image optimization problem effectively requires to compute X that maximizes the above cost function. In general, the cost function may be any function of image quality factors, representing the complicated relations within different quality factors:

$$\text{Cost}(x) = f[Y(x)]$$

Various input-output relations exist in terms of ultrasound image optimization. In a particular embodiment, varying an input (imaging parameter) may affect multiple outputs (image quality factors). Non-limiting examples of inputs include transmit frequency, pulse length, transmit aperture size, receiving frequency and bandwidth as a function of depth, receiving aperture size, pulse repetition frequency (frequency of transmit pulse that is fired sequentially), beam line density (number of beam lines that form an image), and focal zone number and positions of the focal zones. Non-limiting examples of outputs include spatial resolution (including axial and lateral resolution), contrast resolution (partially determined by side lobe levels), penetration, image uniformity, frame rate, and image artifacts (haze, reverberation, etc.).

An input may affect multiple outputs in a complicated manner. In a particular embodiment, a higher transmit frequency may improve spatial resolution, but reduce SNR, penetration, and frame rate. In another embodiment, increasing an aperture size may improve the spatial resolution, but results in degradation of image uniformity and reduction in frame rate. In yet another embodiment, increasing a number of focal zones may improve image uniformity, but reduce frame rate. In one embodiment, a higher pulse repetition frequency may increase frame rate, but cause more acoustic decay reverberation artifacts. Furthermore, for different patient and/or applications, the optimization (or trade-off) may be different. For example, for an easy patient, wherein signal-to-noise ratio and imaging is not a problem, frequency may be increased to improve penetration; while for a difficult patient, wherein signal-to-noise ratio is an issue, frequency may be reduced to ensure an acceptable penetration. In another embodiment, for a fast moving tissue, frame rate may be increased to keep track of the tissue. In such a case, spatial resolution and image uniformity may be sacrificed for a better frame rate and a typical adjustment may be reducing the beam line density and/or reducing the number of focal zones.

It should be noted that embodiments of the invention are not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

Figure 2:
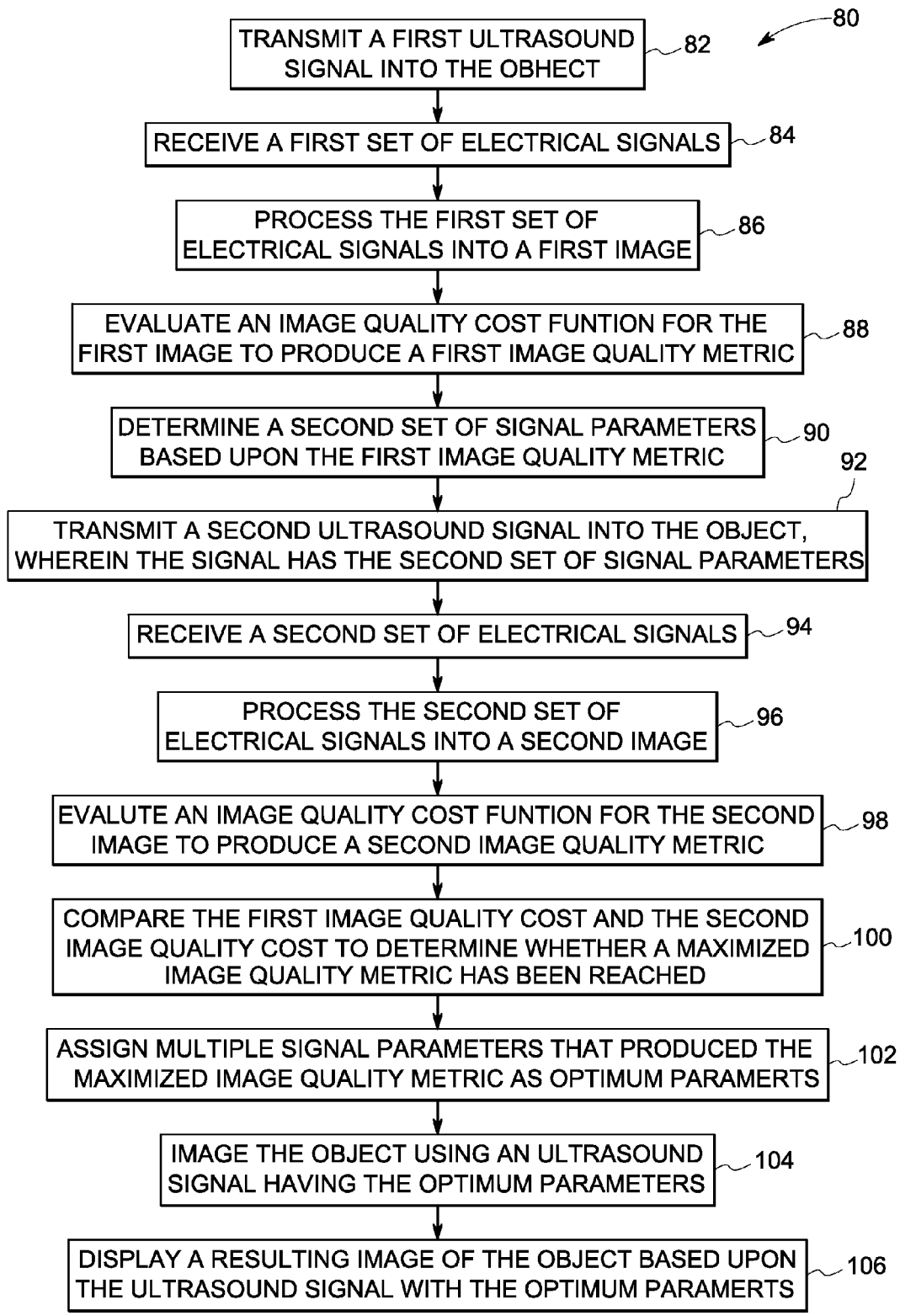
FIG. 2 is a flow chart representing steps in a method for image optimization in ultrasound imaging of an object in accordance with an embodiment of the invention.

FIG. 2 is a flow chart representing steps in a method 80 for image optimization in ultrasound imaging of an object. The method 80 includes transmitting a first ultrasound signal into the object in step 82, wherein the signal has a first set of signal parameters. In a particular embodiment, the ultrasound signal is transmitted via an ultrasound transducer. A first set of electrical signals representing reflections of the first ultrasound signals are received from the object in step 84. The first set of electrical signals are processed into a first image in step 86. In one embodiment, the first set of electrical signals and the second set of electrical signals are processed. An image quality cost function for the first image is evaluated to produce a first image quality metric in step 88. In one embodiment, the image quality cost function is defined as a weighted sum of multiple image quality factors. Non-limiting examples of the image quality factors include spatial resolution, signal-to-noise ratio, frame rate, penetration within the object, and image artifacts. A second set of signal parameters is predicted based upon the first image quality factors in step 90. In a particular embodiment, the prediction of a second set of signal parameters based on the image quality factors of the first set is performed via an intelligent optimization algorithm mimicking experienced ultrasound users. For example, if the quality factor of penetration is lacking in the first set, typically the frequency needs to be decreased. If the frame rate is less than desired, the beam line density needs to be decreased. The intelligent optimization algorithm may be implemented using a framework of decision tree or dynamic programming that is well known by experts in those areas. In one embodiment, the first set of signal parameters and the second set of signal parameters include multiple beamforming parameters and multiple image processing parameters. In another embodiment, the beamforming parameters include at least one of frequency, pulse rate, a transmit aperture size, a receiving aperture size, a pulse repetition frequency, beam line density, a number of focal zones and a position of focal zones. In another embodiment, the image processing parameters include receive filter, gain partition and dynamic range compression.

A second ultrasound signal is transmitted into the object in step 92, wherein the second ultrasound signal has the second set of signal parameters. A second set of electrical signals representing reflections of the second ultrasound signal from the object is received in step 94. The second set of electrical signals is processed into a second image in step 96. An image quality cost function is evaluated for the second image to produce a second image quality metric in step 98. The first image quality metric and the second image quality metric are compared to determine whether a maximized image quality metric has been reached in step 100. Multiple signal parameters that produce the maximized image quality metric are assigned as optimum parameters in step 102. The object is imaged using an ultrasound signal having the optimum parameters in step 104. A resulting image of the object is displayed based upon the ultrasound signal with the optimum parameters in step 106.

Figure 3:
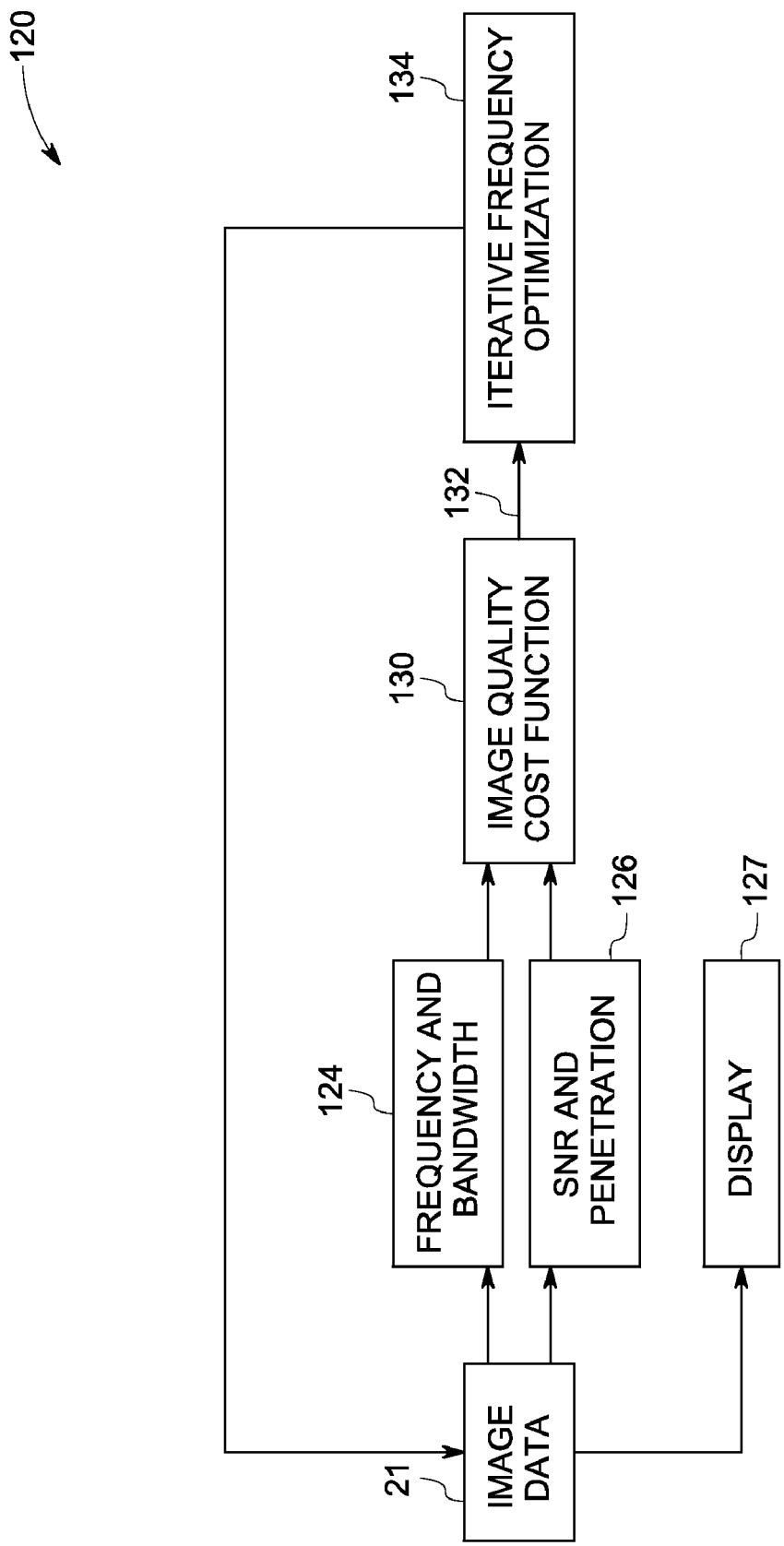
FIG. 3 is a schematic illustration of an exemplary automatic image optimization system that adjusts axial/lateral spatial resolution and signal to noise ratio of an ultrasound image in accordance with an embodiment of the invention.

FIG. 3 is a schematic illustration of an exemplary automatic image optimization system 120 that adjusts transmit waveform setting (frequency and bandwidth) by estimating axial/lateral spatial resolution, signal-to-noise ratio and penetration factor of an ultrasound image data 121 displayed by a display 122. The factors that affect the axial/lateral spatial resolution and signal-to-noise ratio include frequency and bandwidth referenced by numeral 124. As illustrated herein, a temporal frequency and bandwidth 124 and signal-to-noise ratio 126 are estimated based upon an image generated in the processor 28 (FIG. 1). The estimated frequency and bandwidth and signal-to-noise ration are fed into an image quality cost function referenced by numeral 130 that adjusts aperture size to output image 132 with improved axial and lateral resolution and signal-to-noise ratio of the image. In an event of a maximized image quality metric not reached, frequency optimization is performed iteratively as referenced by numeral 134 in a feedback loop. In a particular embodiment, an image frame that contains both signal and noise is received. A noise frame obtained from a zero transmit amplitude containing only noise, is also received. A signal-to-noise ratio 126 is then calculated and fed into the image quality cost function 130.

The various embodiments of a system and method for ultrasound image optimization described above thus provide a way to achieve a convenient and efficient means for optimizing image quality. The technique is also automated thereby eliminating operator dependency. Further, the system and technique allows for cost effective means.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the use of a handheld ultrasonic transducer with respect to one embodiment can be adapted for use with an image quality cost function configured to adjust a frame rate described with respect to another. Similarly, the various features described, as well as other known equivalents for each feature, can be mixed and matched by one of ordinary skill in this art to construct additional systems and techniques in accordance with principles of this disclosure.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A method for automatic image optimization in ultrasound imaging of an object, the method comprising:
   transmitting a first ultrasound signal into the object, the signal having a first plurality of signal parameters;

receiving a first set of electrical signals representing reflections of the first ultrasound signals from the object;

processing the first set of electrical signals into a first image including a set of image quality factors;

evaluating an image quality cost function for the first image to produce a first image quality metric;

determining a second plurality of signal parameters based upon the first image quality metric;

transmitting a second ultrasound signal into the object, the signal having the second plurality of signal parameters;

receiving a second set of electrical signals representing reflections of the second ultrasound signal from the object;

processing the second set of electrical signals into a second image including the set of image quality factors;

evaluating an image quality cost function for the second image to produce a second image quality metric;

comparing the first image quality metric and the second image quality metric to determine whether a maximized image quality metric has been reached;

assigning a plurality of signal parameters that produced the maximized image quality metric as optimum parameters;

imaging the object using an ultrasound signal having the optimum parameters; displaying a resulting image of the object based upon the ultrasound signal with the optimum parameters; and wherein said evaluating comprises computing an image quality cost function, the image quality cost function is defined as a weighted sum of a plurality of image quality factors.

2. The method of claim 1, wherein said transmitting comprises transmitting via an ultrasound transducer.

3. The method of claim 1, wherein said first plurality of signal parameters and said second plurality of signal parameters comprise a plurality of beamforming parameters and a plurality of image processing parameters.

4. The method of claim 3, wherein said beamforming parameters comprise at least one of frequency, pulse length, a transmit aperture size, a receiving aperture size, a pulse repetition frequency, beam line density, number of focal zones and positions of focal zones.

5. The method of claim 1, wherein the image quality factors comprise spatial resolution, signal-to-noise ratio, frame rate, penetration within the object, and image artifacts.

6. The method of claim 1, wherein said processing comprises beamforming the first set of electrical signals and the second set of electrical signals.

7. A system for image optimization in ultrasound imaging of an object, the system comprising:

an ultrasound transducer acoustically coupled to the object, the ultrasound transducer configured to:

transmit a first ultrasound signal and a second ultrasound signal into the object, wherein the first ultrasound signal and the second ultrasound signal comprise a first plurality of signal parameters and a second plurality of signal parameters respectively; and convert a first set of reflected ultrasound signals and a second set of reflected signals from the object into a respective first set of electrical signals and a second set of electrical signals;

a processor coupled to the ultrasound transducer, the processor configured to:

process the first set of electrical signals and the second set of electrical signals into a first image and a second image including a set of image quality factors;

evaluate an image quality cost function for the first image and the second image to produce a first image quality metric and a second image quality metric;

determine the second plurality of signal parameters based upon the first image quality metric;

compare the first image quality metric and the second image quality metric to determine whether a maximized image quality metric has been reached;

assign a plurality of parameters that produced the maximized image quality metric as optimum parameters;

image the object using an ultrasound signal having the optimum parameters;

a display monitor configured to display a resulting image of the object based upon the imaged object from the ultrasound signal with the optimum parameters; and wherein the image quality cost function is defined as a weighted sum of a plurality of image quality factors.

8. The system of claim 7, wherein the ultrasound transducer comprises a handheld ultrasound transducer.

9. The system of claim 7, wherein the object is a living organism.

10. The system of claim 7, wherein the processor is configured to beamform the received first set of electrical signals and the second set of electrical signals.

11. The system of claim 7, wherein the first plurality of parameters and the second plurality of parameters comprise beamforming parameters and image processing parameters.

12. The system of claim 11, wherein said beamforming parameters comprise at least one of frequency, pulse length, a transmit aperture size, a receiving aperture size, a pulse repetition frequency, beam line density, number of focal zones and positions of focal zones.

13. The system of claim 11, wherein said image processing parameters comprise receive filter, gain partition and dynamic range compression.

14. The system of claim 7, wherein the image quality factors comprise spatial resolution, signal-to-noise ratio, frame rate, penetration within the object, and image artifacts.

* * * * *